United States Patent
Krüger et al.

(10) Patent No.: US 11,135,382 B2
(45) Date of Patent: Oct. 5, 2021

(54) MEDICAL DEVICE AND PROCESS FOR ALARM ORGANIZATION

(71) Applicant: Drägerwerk AG & Co. KGaA, Lübeck (DE)

(72) Inventors: Thomas Krüger, Reinfeld (DE); Birger Landwehr, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 516 days.

(21) Appl. No.: 15/623,815

(22) Filed: Jun. 15, 2017

(65) Prior Publication Data

US 2017/0361043 A1      Dec. 21, 2017

(30) Foreign Application Priority Data

Jun. 16, 2016   (DE) .................... 10 2016 007 336.5

(51) Int. Cl.
  *A61M 16/00*  (2006.01)
  *A61M 16/08*  (2006.01)
  *A61M 16/20*  (2006.01)

(52) U.S. Cl.
  CPC .... *A61M 16/0051* (2013.01); *A61M 16/0069* (2014.02); *A61M 16/024* (2017.08); *A61M 16/0816* (2013.01); *A61M 16/208* (2013.01); *A61M 2016/0027* (2013.01); *A61M 2016/0039* (2013.01); *A61M 2016/0042* (2013.01); *A61M 2205/0294* (2013.01); *A61M 2205/18* (2013.01); *A61M 2205/3334* (2013.01); *A61M 2205/3344* (2013.01); *A61M 2205/3348* (2013.01);

(Continued)

(58) Field of Classification Search
  CPC ............ A61M 16/0051; A61M 16/022; A61M 16/024; A61M 16/026; A61M 16/0069; A61M 16/0816; A61M 16/085; A61M 16/0875; A61M 16/208; A61M 2016/0027; A61M 2016/003; A61M 2016/0021; A61M 2016/0036; A61M 2205/18

See application file for complete search history.

(56) References Cited

U.S. PATENT DOCUMENTS 2,904,035 A   9/1959   Andreasen
5,400,777 A   3/1995   Olsson et al.
         (Continued)

FOREIGN PATENT DOCUMENTS

DE   10 2005 061 439 B3   5/2007
EP        2 869 427 A1    5/2015
         (Continued)

OTHER PUBLICATIONS

Norm DIN EN ISO 80601-2-12.

*Primary Examiner* — Kendra D Carter
*Assistant Examiner* — Brian T Khong
(74) *Attorney, Agent, or Firm* — McGlew and Tuttle, P.C.

(57) ABSTRACT

A medical device is provided with an alarm organization. A process for alarm organization of a medical device is also provided. Based on pressure measured values and flow measured values and with a comparison criterion, it is determined whether an elevation of an airway pressure of an anesthesia device or of a ventilator is caused by a coughing event. A visual and/or acoustic output of a warning or alarm is adapted, indicating the elevated airway pressure $P_{AW\_High}$.

20 Claims, 2 Drawing Sheets (52) U.S. Cl.
CPC . *A61M 2205/581* (2013.01); *A61M 2205/583* (2013.01); *A61M 2230/40* (2013.01)

(56) References Cited

U.S. PATENT DOCUMENTS

| | | | |
|---|---|---|---|
| 5,937,853 | A | 8/1999 | Ström |
| 6,553,990 | B2 | 4/2003 | Hoffmann |
| 6,571,792 | B1 | 6/2003 | Hendrickson et al. |
| 7,445,609 | B2 | 11/2008 | Bunke et al. |
| 7,882,835 | B2 | 2/2011 | Eger et al. |
| 2005/0179536 | A1* | 8/2005 | Lederer, IV ............ G08B 7/06 340/506 |
| 2008/0178880 | A1* | 7/2008 | Christopher ...... A61M 16/0051 128/204.23 |
| 2011/0125044 | A1* | 5/2011 | Rhee .................... A61B 5/113 600/534 |
| 2011/0175728 | A1* | 7/2011 | Baker, Jr. ......... A61M 16/0051 340/540 |
| 2011/0197885 | A1* | 8/2011 | Wondka ................... A61B 5/03 128/204.22 |
| 2012/0000464 | A1* | 1/2012 | Gajic ..................... A61B 5/091 128/202.22 |
| 2012/0103333 | A1* | 5/2012 | Dingley ............... A61M 16/00 128/203.28 |
| 2012/0209089 | A1* | 8/2012 | Garde ................... A61B 5/103 600/301 |
| 2012/0283581 | A1* | 11/2012 | Oide .................... A61B 5/0816 600/485 |
| 2013/0125883 | A1* | 5/2013 | Bonassa ............ A61M 16/0057 128/202.22 |
| 2013/0255691 | A1* | 10/2013 | Mansfield ......... A61M 16/0051 128/207.14 |
| 2013/0263855 | A1* | 10/2013 | Tivig ................... A61B 5/4839 128/204.23 |
| 2014/0276166 | A1* | 9/2014 | Drori .................. A61B 5/0531 600/529 |
| 2015/0258290 | A1* | 9/2015 | Landwehr .......... A61M 16/021 128/202.22 |
| 2016/0136370 | A1* | 5/2016 | Heesch ............. A61M 16/0003 128/204.23 |
| 2017/0164871 | A1* | 6/2017 | Ramanan ............... A61B 5/087 |
| 2017/0325735 | A1* | 11/2017 | Brand ................ A61M 16/024 |
| 2017/0368410 | A1* | 12/2017 | Brand ............... A61M 16/0096 |

FOREIGN PATENT DOCUMENTS

| | | |
|---|---|---|
| WO | 2007/085110 A1 | 8/2007 |
| WO | 2008/098382 A1 | 8/2008 |

\* cited by examiner

MEDICAL DEVICE AND PROCESS FOR ALARM ORGANIZATION

CROSS REFERENCE TO RELATED APPLICATIONS

This application claims the benefit of priority under 35 U.S.C. § 119 of German Application 10 2016 007 336.5, filed Jun. 16, 2016, the entire contents of which are incorporated herein by reference.

FIELD OF THE INVENTION

The present invention pertains to a medical device with an alarm organization as well as a process for alarm organization in case of a medical device. The medical device can be configured as an anesthesia device, as a ventilator for adult patients or children, as an emergency ventilator for a use in rescue or search missions on land, on water or in the air or as an especially, so-called neonatal ventilator for ventilating newborns. Medical devices for ventilating a patient are known from the state of the art. For example, there are the above-mentioned ventilators, emergency ventilators, neonatal ventilators, as well as also anesthesia devices, which make it possible to ventilate patients mechanically—mandatorily or in an assisted manner. Ventilators are preferably used on intensive care units for treating patients, in whom the possibility for supplying breathing air and oxygen, as well as for removing carbon dioxide is minimized or limited by the patient's own breathing activity. Ventilators for carrying out a mechanical ventilation according to the state of the art are described in U.S. Pat. Nos. 2,904,035, 5,400,777, 5,937,853, and WO 2007/085110 A1.

BACKGROUND OF THE INVENTION

Anesthesia devices are used for the duration of an operation to supply a patient with anesthetics, so that an anesthetic effect can be reached at the patient. In addition, the anesthesia device also takes over the mechanical ventilation of the patient because the possibility of an own breathing activity is no longer present for the patient due to the anesthetic effect. Anesthesia devices for carrying out an anesthesia on human beings or animals according to the state of the art are described in WO 2008/098382 A1, U.S. Pat. Nos. 6,571,792, and 6,553,990.

Inadmissible operating states must be avoided for the operation of medical devices, and especially of ventilators and anesthesia devices.

The way to classify which operating states are unsafe and which operating states are to be avoided are regulated in the area of medicine by regulations or standards, such as, for example, the standard ISO 80601-2-12.

It appears from the standard ISO 80601-2-12 that an inadmissibly high airway pressure should be avoided at the patient and that a ventilator should signal this value to the user by means of an alarm. In this case, a signaling can be embodied as an acoustic or optical alarm or as a combination of an optical and acoustic alarm. In addition, the alarm from the ventilator or from the anesthesia device or from the medical device that is set up and configured for ventilating a patient can be forwarded to a higher level analysis system.

In case of an elevation of the airway pressure $P_{AW}$ above a predefined pressure threshold value, a suitable action is taken by the medical device to reliably prevent a risk to the patient, for example, due to a further rise in pressure. For this purpose, for example, the following actions or means are implemented in the medical device for a pressure relief, such as an immediate switching off of the inspiratory dispensing of breathing gas, an opening of the exhalation valve in the exhalation branch, i.e., in the gas routing system (connection system, ventilation tube) for transporting breathing gases from the patient or an opening of a safety valve in the inhalation branch, i.e., in the gas routing system (connection system, ventilation tube) for dispensing breathing gases to the patient.

U.S. Pat. No. 7,882,835 B2 as well as DE 10 2005 061 439 B3 show a device and process for determining the leaks of a ventilator. In this case, FIG. 1 in U.S. Pat. No. 7,882,835 B2 shows a basic configuration of a ventilator with connection to a patient as an example. An inhalation branch, an exhalation branch, as well as connections to the patient and a measuring site at the patient are shown. By means of an analysis of volume, volume flow and pressure measured signals, especially in association with time intervals of an inhalation and an exhalation, it is determined using a model approach whether leaks are present during the ventilation. Hence, these documents show that it is possible by means of an analysis of measured signals to determine states, such as leak states during the ventilation in this case and to carry out a monitoring based thereon. If such a monitoring of a ventilator is used during the ventilation of a patient, then the safety of the ventilation increases, on the one hand, and the monitoring in cases in which leaks cannot be unambiguously identified under defined conditions results in an alerting of a deficient state, even though the state does not have to be classified as being deficient in each case, on the other hand.

U.S. Pat. No. 7,445,609 B2 as well as DE 10 2005 061 439 B3 show a device for controlling the feed of an active ingredient. This medical device for feeding an active ingredient shown in these documents corresponds to an anesthesia device, which is configured to dispense or to deliver active ingredient concentrations by means of a dispensing unit, for example, with a so-called anesthetic dispenser (Vapor) in a controlled manner or in a control circuit to a patient.

It is ensured by means of a safety device in connection with a patient model that maximum active ingredient concentrations can be monitored and thus inadmissible overdoses can be prevented.

In clinical practice, alarms play a large role in guaranteeing the health and safety of the patient.

However, it is problematic when the clinical staff is needlessly burdened because of false alarms and because of the sound level and loudness due to an acoustic alarm, since the real alarms cannot thereby be adequately operated under certain marginal conditions, on the one hand, and the trust in the alarm for the alerted alarm situation declines among the clinical staff, on the other hand. Hence, it is highly essential that the number of falsely alerted alarm situations as well as false alarms be as small as possible.

Standard ISO 80601-2-12 makes it possible to analyze situations with an elevated airway pressure as to whether the elevation of the airway pressure was caused by an activity of the patient or as to whether other circumstances or modes of operation in the medical device for mechanical ventilation (ventilator) are the cause of the elevation of the airway pressure.

Depending on this analysis, ISO 80601-2-12 allows alerting a highly elevated or elevated airway pressure, when it was caused by the patient, in a different way than elevated airway pressures that were caused by the medical device for ventilation (ventilator).

In this case, another way of alerting can be configured, for example, as an alarm with a reduced or markedly reduced loudness.

An elevation of the airway pressure $P_{AW}$ may have a variety of the following causes mentioned as examples in a list here.

Disturbances in the Dispensing of Breathing Gas:
Disturbances in the regulation of flow, volume or pressure in the medical device for ventilating a patient or in a ventilator or in an anesthesia device are possible causes for an alarm, which indicates an elevation of the airway pressure. A cause for such disturbances may be, for example, mechanical or pneumatic components, such as valves or dispensing units, which have a malfunction. In such cases, the medical device sounds an alarm in case an elevation of the airway pressure is indicated. In terms of troubleshooting, a replacement of components in the medical device is usually necessary in such cases.

Blockages in the Gas Supply:
Another cause for elevations of the airway pressure may be a compromise in the gas-routing components. Gas-routing components, for example, tube systems or tubes route the breathing air to the patient and again away from there. Tube systems may be configured as so-called two-tube systems, wherein one breathing tube routes inspiratory breathing gas to the patient and another breathing tube routes expiratory exhaled breathing gas from the patient to the ventilator or anesthesia device. By contrast, in a one-tube system, only an inspiratory breathing tube is present for supplying breathing gas to the patient, the exhaled breathing gas is exhaled in that case directly from the patient into the surrounding area, usually via a discharge valve arranged at the patient. A blockage or kink in a tube may, for example, lead to an elevated ventilation pressure building up in front of the kink point. This elevated ventilation pressure is then acting directly on the patient, in case the blockage (kink point) is located in the expiratory gas carrying away from the patient. Such a state represents a high risk for the patient and must be detected and alerted by the medical device, so that this state can be remedied as quickly as possible by the clinical staff. In addition, the actions described above for pressure relief are then effective in the medical device in such operating situations. A blockage in the inspiratory gas carrying away to the patient can, on the other hand, bring about a gas deficiency at the patient.

Accumulations of Condensation:
In a manner similar to how kink points in the tube have an effect on pressure ratios in the tube, or at the patient, accumulations of water, which may form due to condensations of humidified breathing air, as well as due to the moist exhaled air in the tube, also have an effect such that an elevation of the airway pressure is possible.

Collections of Secretion:
Another possibility for an elevation of the airway pressure is a possible closure of an endotracheal tube used for ventilation, which is introduced into the trachea of the patient via the oral cavity. For example, the air flow into the patient and out again can be blocked by a biting down.

Such a biting down occurs, for example, due to cramping of the muscles of the patient. Another possibility for a closure of the endotracheal tube arises due to accumulations of secretion, the so-called mucus in the endotracheal tube. Such accumulations increase the flow resistance in the endotracheal tube and thus lead to an elevation of pressure.

In this connection, secretion in the airway is designated as mucus, which is transported from the patient partly with the exhalation or by means of coughing from the airway. An irritation of the throat in the patient may be triggered by an accumulation of secretion or mucus.

Counter Breathing:
Another possibility for an elevation of pressure, which leads to an elevated airway pressure, is the so-called counter breathing of the patient. Spontaneous breathing that is counter breathing designates the state that the medical device delivers air to the or into the patient for carrying out the mechanical ventilation, but the patient tries to exhale, i.e., breathe in opposition to the prevailing flow of the mechanical ventilation—counter breathing—at the same time. In this connection, the patient and the ventilator are not synchronous with one another in the phases of inhalation and exhalation (inspiration/expiration). Such a state is quite strenuous for the patient; hence, such a state should be avoided as much as possible. An avoidance is present in the form of setting limits for the alarm in case of an elevation of an airway pressure such that such states with elevated airway pressure, caused by counter breathing, are preferably already alerted in case of a slight elevation of pressure.

User Interaction:
Other causes for elevations of the airway pressure are the so-called machine-induced or user-induced alarm situations. Machine- or user-induced alarms arise due to setting procedures by the user, i.e., that an increase in pressure may occur in case of changes in limit values, changes in pressure and volume values, so that an alarm for an elevated airway pressure comes about by the setting procedures being carried out chronologically offset to one another, or not yet being entirely concluded and all set values not yet being coordinated with one another. Overshooting in the control circuit for a short time and thus fluctuations of pressure or elevations of pressure may also occur in the case of these settings. These overshoots are due to the setting procedures themselves and are present only briefly during the setting procedure and then no longer play a role in the further ventilation operation of the device.

Coughing Event
Besides the situations mentioned, in which an alarm generation for an elevated airway pressure in a medical device may occur from various constellations, there are alarms that are induced by the patient for an elevated airway pressure. Thus, an irritation of the throat may, for example, develop at the patient undergoing ventilation in certain situations, for example, triggered by the above-described counter breathing or due to secretion in the airway. Such an irritation of the throat or even cough reflex is independent of whether the breathing phase just at this time is an inhalation phase or an exhalation phase, in any case an event, in which an additional quantity of exhaled breathing gas with the cough reaches the tube system abruptly, as a pulse, so to speak and thus an increased flow rate flows from the patient. This pulse-like increased flow rate then results in a massive rise in pressure or transient pressure event occurring for a brief time. This rise in pressure is detected and an alarm is triggered. An alarm, which indicates an elevated airway pressure, is triggered. A cough or cough attack is frequently observed if the secretion that is collected from the bronchi or the lower and upper airway triggers a cough reflex during a recovery phase, for example, after a surgical procedure. Even though the cough itself in many cases does not mean any immediate risk to the patient, the staff is alerted by the triggered alarm for an elevated airway pressure.

SUMMARY OF THE INVENTION

An object of the present invention is to provide a medical device with an alarm organization, as well as a process for an alarm organization in case of a medical device.

Provisions are made according to the present invention for present measured values from sensors in a medical device, which is suitable and configured for a ventilation of a patient or of living beings, being used to detect whether a coughing event is indicated. If such a coughing event is indicated, it is possible, as is described in standard ISO 80601-2-12, to manage alarms that indicate an elevated airway pressure in cases, in which this elevation of the pressure was caused by the patient, in a different way than alarms, in which the cause of the pressure elevation is not caused by the patient.

The medical device, on which the process for alarm organization is being executed, is preferably configured as an anesthesia device or a ventilator.

For an analysis of the situation and for differentiation of whether an elevation of the pressure caused by the patient is present as the cause for an alarm of an elevated airway pressure, pressure sensors and flow sensors, which are located in or at the medical device or are arranged at this device in or at gas-routing components or connection systems, such as, for example, tube systems, are provided for analysis.

Table 1 below shows measuring sites of the medical device for the ventilation of a patient, at which pressure measurements and flow measurements can be developed, from which both conditions of the airway pressure as well as conditions of the patient flow rate are possible.

Three suitable measuring sites for pressure measurement and flow measurement, which are different from one another in principle, an inspiratory measuring site and an expiratory measuring site within the medical device for ventilating a patient, as well as a measuring site near the patient (Y-piece), outside of and proximal to the medical device for ventilating a patient, are mentioned in Table 1.

The measured values that can be detected at these measuring sites as well as the measured quantities that can be derived, calculated or determined from these detectable measured quantities, are shown.

The object is accomplished by a process for alarm organization according to the present invention in case of a medical device according to a first aspect of the present invention.

The medical device is preferably configured as an anesthesia device or as a ventilator. The process according to the present invention is configured to detect coughing events of a patient and to adapt the alarm on the basis thereof. The medical device is configured to process sensor signals provided by sensors arranged in or at measuring sites of the medical device or sensor signals which are provided by sensors which are associated with the medical device as associated measuring sites. The sensor signals indicate pneumatic/fluidic physical states of a breathing gas in a gas-routing connection system from and to the patient, which system is connected and coupled in a gas-routing manner to the medical device and to a patient and is configured for transporting gases.

Values of an airway pressure $P_{AW}$ present in the gas-routing connection system and of a flow rate flowing in the gas-routing connection system, as well as flow directions corresponding to the flow rate in the gas-routing connection system can be determined from the sensor signals.

The process for alarm organization according to the present invention uses these sensor signals to determine the airway pressure $P_{AW}$, as well as to determine whether in connection with changes in the airway pressure $P_{AW}$, for example, an elevation of the airway pressure $P_{AW}$, an event caused by the patient with a flow rate change, especially an elevation of the flow rate and/or of the airway pressure $P_{AW}$ caused by the patient caused by a coughing event or a cough attack of the patient is indicated or present.

In case it is determined by means of the process for alarm organization according to the present invention that the elevation of the airway pressure $P_{AW}$ is brought about or caused by a coughing event or cough attack by the patient, the type of alarm for the elevation of the airway pressure $P_{AW}$ can be varied by the ventilator according to standard ISO 80601-2-12, compared to a situation, in which the elevation of the airway pressure $P_{AW}$ cannot be causally attributed to the patient.

In the process for alarm organization in case of a medical device, the following steps are carried out:

Comparison based on the determined values of the flow rate and the determined flow directions whether an exceeding of a comparison criterion indicating the airway pressure $P_{AW}$ is indicated by the determined value of the airway pressure $P_{AW}$ and setting of an alarm criterion indicating an elevated airway pressure $P_{AW\_High}$ based on the comparison,

TABLE 1

| Measuring site | Detected pressure measured value | Determinable pressure measured quantity | Detected flow measured value | Determinable flow measured quantity |
| --- | --- | --- | --- | --- |
| Inspiratory (inhalation) | Inspiratory pressure $P_{insp}$ | $P_{aw} = P_{insp} - P_{hose\_insp}$ | Inspiratory flow rate $\dot{V}_{insp}$ | |
| Expiratory (exhalation) | Expiratory pressure $P_{exp}$ | $P_{aw} = P_{exp} - P_{hose\_exp}$ | Expiratory flow rate $\dot{V}_{exp}$ | $\dot{V}_{Pat} = \dot{V}_{exp} - \dot{V}_{insp}$ |
| Near the patient (proximally) | Patient pressure $P_{Pat}$ | $P_{aw} = P_{Pat}$ | Patient flow rate $\dot{V}_{Pat}$ | $\dot{V}_{Pat}$ Rate & direction | in case the exceeding of the comparison criterion indicating the airway pressure $P_{AW}$ is indicated by the determined value of the airway pressure $P_{AW}$, determination of whether the medical device is in an operating state, in which a smaller quantity of breathing gas is being fed from the medical device to the patient than is flowing from the patient based on a comparison of whether an exceeding of a comparison criterion indicating a patient flow rate and a flow direction is indicated by the determined value of the flow rate and by the determined flow direction, resetting of the alarm criterion indicating the elevated airway pressure $P_{AW\_High}$, in case the exceeding of the comparison criterion indicating for the patient flow rate and the flow direction is indicated by the determined values of the flow rate and of the flow direction, and that the medical device is in the operating state, in which a smaller quantity of breathing gas is being fed to the patient by the medical device than is flowing from the patient, adaptation of a visual and/or acoustic output of a warning or alarm indicating the elevated airway pressure $P_{AW\_High}$ based on the alarm criterion.

A possible comparison criterion for the comparison criterion indicating the airway pressure $P_{AW}$ is a predefined pressure threshold value.

A pressure value above a pressure threshold value, for example, of 30 hPa±3 hPa, thus characterizes an elevated airway pressure $P_{AW\_High}$ for an adult patient.

A possible comparison criterion for the comparison criterion indicating the patient flow rate and the flow direction is a predefined flow rate threshold value connected with a flow direction. Thus, for example, a flow rate above a flow threshold value, for example, of approx. 2.5 L/min±0.2 L/min, with a corresponding flow direction from the patient, characterizes an operating state with exhalation of the patient.

Thus, a flow rate above a flow threshold value, for example, of 1.5 L/min±0.2 L/min, along with a corresponding flow direction towards the patient, characterizes an operating state with inhalation of the patient.

Thus, for example, a flow rate below a flow threshold value, for example, of 2.5 L/min±0.2 L/min, with a corresponding flow direction from the patient, characterizes an end of an exhalation or an expiratory pause.

Thus, for example, a flow rate below a flow threshold value, for example, of 1 L/min±0.2 L/min, with a corresponding flow direction towards the patient, characterizes a beginning or an end of an inhalation or an inspiratory pause.

The operating state, in which a smaller quantity of breathing gas is being fed by or flows from the medical device by means of an inspiratory ventilation tube towards the patient than is flowing from the patient and, for example, flows back into the medical device via an expiratory ventilation tube, corresponds in this case to an operating state of an exhalation of the medical device.

This operating state of exhalation represents a situation, in which an additional quantity of exhaled breathing gas due to a coughing event or cough attack is indicated as an at least temporary elevation of the flow rate in the gas-routing connection system and brings about an elevated airway pressure $P_{AW\_High}$.

Another operating state, in which an equal or smaller quantity of breathing gas is being fed by or is flowing from the medical device by means of an inspiratory ventilation tube to the patient than is flowing from the patient and, for example, flows back into the medical device via an expiratory ventilation tube, corresponds in this case to an operating state of an inhalation of the medical device with a simultaneous exhalation activity of the patient as it is possible, for example, in case of the so-called "counter breathing" described above.

This operating state of inhalation represents a situation, in which an additional quantity of exhaled breathing gas due to spontaneous breathing is indicated as an at least temporary elevation of the flow rate in the gas-routing connection system and brings about an elevated airway pressure $P_{AW\_High}$.

This at least temporary elevation of the flow rate, as an indication of the operating state, in which a smaller quantity of breathing gas is being fed to the patient than is flowing from the patient, is determined based on the sensor signals of the pressure sensor and flow sensor, the measuring sites of which in or at the medical device, or in or at the gas-routing connection system are shown in Table 1.

An alarm criterion can in this case be configured as a status code (Flag), a status marker (Pointer) or a status variable, which in the process for alarm organization is set (SET), is reset (RESET), as well as is polled and used for controlling the alarm organization and/or the process.

In a special embodiment of the process, the acoustic output of the warning or alarm is suppressed or is muted as an adaptation of the output of the warning or alarm in case before the alarm criterion indicating the elevated airway pressure $P_{AW\_High}$ is reset.

Thus, it is obvious to the user that an alarm situation is indicated, the alarm state is maintained at the device, only the acoustic output is suppressed in this case. The visual output of the warning on the display screen signals to the user that the alarm criterion had indeed existed, but that it was reset because the situation was considered to be a coughing event.

In a special embodiment of the process, the visual output of the warning or alarm is suppressed as an adaptation of the output of the warning or alarm in case before the alarm criterion indicating the elevated airway pressure $P_{AW\_High}$ is reset.

Thus, it is made possible, for example and advantageously, to carry out a prioritization of the alarm output, when, for example, besides the coughing event, other, more urgent alarms are at the same time due to signal or alert the coughing event secondarily.

In a special embodiment of the process, a time delay takes place in the visual and/or acoustic output of the warning or alarm as an adaptation of the output of the warning or alarm based on the alarm criterion. Thus, it is made possible, for example and advantageously, to carry out a prioritization of the alarm output, when, for example, besides the coughing event, other, more urgent alarms are at the same time due to signal or alert the coughing event with a time delay and secondarily, when, for example, situations, which indicate the more urgent alarms, are no longer indicated.

In a special embodiment of the process, both a suppression of the visual output of the warning or alarm and a muting of the acoustic output of the warning or alarm take place as an adaptation of the output of the warning or alarm based on the alarm criterion. This results in a complete suppression of a $P_{AW\_High}$ alarm caused by the patient, as standard ISO 80601-2-12 makes it possible, in case of a coughing event.

In a special embodiment of the process, no delay takes place in the visual and/or acoustic output of the warning or alarm as an adaptation of the output of the warning or alarm based on the alarm criterion, when the alarm criterion is obsolete and/or a valid reset criterion is indicated for the alarm indicating the elevated airway pressure $P_{AW\_High}$.

In a special embodiment of the process, a check is carried out as to whether a configuration of the medical device or adaptations of settings for controlling the ventilation at the medical device are currently or essentially simultaneously taking place before the setting or before the resetting of the alarm criterion indicating the elevated airway pressure $P_{AW\_High}$ and, in case a configuration of the medical device is taking place or adaptations of settings for controlling the ventilation at the medical device are taking place, no setting or no resetting of the alarm criterion is carried out.

In a special embodiment of the process, a state of an exhalation valve or a control signal for such an exhalation valve is taken into consideration for detecting a breathing phase and determining whether the medical device is in an operating state of an exhalation.

The embodiments described represent each alone, as well as in combination or combinations with one another, special configurations of the process for alarm organization according to the present invention in case of a medical device, which is preferably configured as an anesthesia device or a ventilator. Here, all further, possible embodiments resulting due to a combination or combinations of a plurality of embodiments and the advantages thereof are also, nevertheless, covered by the idea of the present invention, even if not all possibilities of combinations of embodiments are mentioned each in detail for this.

The above-described embodiments of the process according to the present invention may also be configured in the form of a computer-implemented process as a computer program product with a computer, wherein the computer is prompted to execute the above-described process according to the present invention, when the computer program is executed on the computer or on a processor of the computer or a so-called "embedded system" as part of a medical device.

In this case, the computer program may be stored on a machine-readable storage medium as well. In an alternative embodiment, a storage medium may be provided, which is intended for storing the above-described, computer-implemented process and is readable by a computer. It lies within the scope of the present invention that not all steps of the process have to be inevitably executed on one and the same computer entity, but rather they may also be executed on different computer entities. The sequence of the process steps may optionally be varied as well. Furthermore, it is possible that individual segments of the above-described process may be executed in a separate unit, which can be sold separately, for example.

The means for accomplishing the object was described above in reference to the process claimed as a first aspect of the present invention. In addition to this, a medical device according to the present invention, which is configured to execute the process according to the present invention in the sense of at least one of the embodiments described, appears as an another aspect. The features mentioned, advantages described or alternative embodiments for the process can likewise also be extrapolated to the other objects claimed and vice versa. The corresponding functional features of the process are in this case configured by corresponding concrete modules of a device, especially by hardware components (µC, µP, DSP, FPGA, ASIC, GAL, logic components), which can be implemented, for example, in the form of a processor (µP), a plurality of processors or in the form of instructions in a memory area, which are processed by the processor. The advantages which are described for the process according to the present invention can be achieved in the same way or in a similar way with the device according to the present invention. Furthermore, the embodiments described and the features thereof and advantages of the process can be extrapolated to the device, and the described embodiments of the device can be extrapolated to the process.

According to the other aspect of the present invention, the object according to the present invention is also accomplished by a medical device with an alarm organization.

Configured as an anesthesia device or ventilator, this medical device is configured for a mechanical, mandatory or assisted ventilation of a patient and has, for this, according to the present invention, a connection system configured for transporting breathing gases, a pressure measuring unit, a flow measuring unit, a control unit, a dispensing unit and an alarm unit. The control unit is in this case preferably configured as a microprocessor module (µC) with an associated internal and/or external memory (RAM).

The flow measuring unit, as well as the pressure measuring unit, are configured for a conversion of electrical signals or data indicating physical measured quantities, which are provided by the flow rate sensor and pressure sensor in data signals suitable for a data processing. In the usual configurations of anesthesia devices and ventilators, the flow measuring unit, the pressure measuring unit and the alarm unit are configured as components or modules of the control unit.

The alarm unit is configured to provide a visual notice, a warning, a message or an acoustic alarm. The control unit is configured in a suitable manner, preferably by means of an interface, to receive pressure measured values and flow measured values, preferably from the pressure measuring unit and from the flow measuring unit or to input via a data link.

Furthermore, the alarm unit is preferably configured to provide or to output a status signal, which indicates an alarm state, at an interface. The connection system has an expiratory path, which is configured and intended for carrying an expiratory quantity of breathing gas away from the patient. The connection system has an inspiratory path, which is configured and intended for bringing an inspiratory quantity of breathing gas from the medical device to the patient. The connection system has a patient connection path, for example, configured as a patient gas supply line in the form of an endotracheal tube that is configured and intended for bringing the inspiratory quantity of breathing gas from the medical device to the patient and for carrying the expiratory quantity of breathing gas away from the patient. The expiratory path and the inspiratory path are connected to each other and to the patient connection path by means of a connection component. The connection component can in this case and is often in practice configured as a so-called Y-piece.

The flow measuring unit has at least one flow sensor, which is arranged in or at the connection system or in or at the medical device and is intended for detecting at least one flow rate measured value of a quantity of breathing gas, which flows from the patient in the connection system or flows from the medical device to the patient.

The flow measuring unit is configured to provide this at least one flow rate measured value to the control unit.

The pressure measuring unit has at least one pressure sensor, which is arranged in or at the medical device or in or at the connection system and is intended for detecting a pressure measured value of a pressure, which is present in the connection system and the pressure measuring unit is configured to provide this at least one pressure measured value to the control unit.

For this purpose, the control unit is suitably configured to compare the detected pressure measured value with a predefined pressure threshold value and to assess based on the comparison whether the detected pressure measured value indicates an elevated airway pressure $P_{AW\_High}$.

The control unit is suitably configured in conjunction with the dispensing unit to control or regulate an arrangement of valves in a suitable manner to let a procedure of a ventilation become effective with pressure control or volume control, monitorings of limit values for pressures and volumes with embodiment of a ventilation rate and durations (I:E) of inhalation phase and exhalation phase by means of the medical device at the patient.

For this purpose, the control unit is further configured to compare the at least one detected flow rate measured value with a predefined flow rate threshold value and to assess based on the comparison whether the at least one flow rate measured value exceeds a predefined flow rate threshold value.

The pressure and flow threshold values are in this case provided to the control unit by the memory.

Thus, the control unit is prepared and configured to activate an alarm criterion, which indicates the elevated airway pressure $P_{AW\_High}$, in case the at least one flow rate measured value exceeds the predefined flow rate threshold value and in case the detected pressure measured value exceeds the predefined pressure threshold value.

For this purpose, the control unit is further configured to assess whether the at least one flow rate measured value and the corresponding flow direction indicate an operating state with a patient flow rate and with a flow direction corresponding to the patient flow rate, in which the quantity of breathing gas flowing to the patient is smaller than the quantity of breathing gas flowing from the patient, i.e., an operating state with a phase of an exhalation of breathing gases is indicated.

The control unit is further configured to validate the alarm criterion, which indicates the elevated airway pressure $P_{AW\_High}$, to the extent that the alarm criterion is activated or remains only in situations, during which no breathing gases are being exhaled by the patient.

For this purpose, the control unit is configured to deactivate the alarm criterion, which indicates the elevated airway pressure $P_{AW\_High}$, in case the at least one flow rate measured value exceeds the predefined flow rate threshold value and the pressure measured value exceeds the predefined pressure threshold value for a predefined time, and the operating state is indicated, in which the quantity of breathing gas flowing towards the patient is smaller than the quantity of breathing gas flowing from the patient from the medical device, during this time.

In this case, a time, in which the control unit has received at least one reliable flow rate measured value sent from the flow measuring unit and at least one pressure measured value sent from the pressure measuring unit, is, for example, preferably selected as the predefined time.

The control unit is further configured for an activation and/or a deactivation of the alarm unit for an output of an alarm of a visual and/or acoustic warning or alarm on the basis of the alarm criterion, indicating the elevated airway pressure $P_{AW\_High}$.

Hence, the medical device is configured, for this, by means of the control unit to assess whether the at least one flow rate measured value indicates an operating state with a patient flow rate and with a flow direction corresponding to the patient flow rate, in which the quantity of breathing gas flowing from the medical device to the patient is smaller than the quantity of breathing gas flowing from the patient and in this case to prompt a deactivation of the alarm unit in reference to the visual and/or acoustic warning or alarm indicating the elevated airway pressure $P_{AW\_High}$. Hence, the control unit is configured to assess whether an operating state, in which a smaller quantity of breathing gas is being fed by or flows from the medical device to the patient by means of the inspiratory path of the connection system than flows from the patient by means of the expiratory path of the connection system, is present.

This operating state corresponds in this case to an operating state of an exhalation in the operation of the medical device, i.e., in general as a rule, of a phase of an exhalation of the patient. The operating state of the exhalation in the operation of the medical device represents an operating state, in which, due to a coughing event or a cough attack, an additional quantity of breathing gas is indicated as an at least temporary elevation of the flow rate in the gas-routing connection system, and the exceeding of the predefined pressure threshold value by the pressure measured value was caused by the coughing event or the cough attack and hence a deactivation of the visual and/or acoustic warning or alarm indicating the elevated airway pressure $P_{AW\_High}$ is permissible and possible under the boundary conditions of standard ISO 80601-2-12.

This at least temporary elevation of the flow rate as an indication of the operating state of exhalation of the medical device and/or coughing event or cough attack is determined on the basis of the sensor signals of the pressure sensor and flow sensor, the measuring sites of which in or at the medical device or in or at the gas-routing connection system are shown in Table 1.

Another situation in the operation of the medical device, which is partially and temporarily different under certain boundary conditions thereof, in which a smaller quantity of breathing gas is being fed or flows to the patient by means of the inspiratory path of the connection system than is flowing from the patient by means of the expiratory path of the connection system, is then indicated when, for example, a blockage of the inspiratory path is present during an inhalation phase of the medical device, wherein, due to a simultaneous exhalation, an exhalation strain or counter breathing of the patient at the same time, an elevation of the airway pressure may also be indicated. In case of a purely mandatory ventilation control, the operating state of the exhalation of the medical device is identical to the exhalation phase of the patient; a smaller quantity of breathing gas then flows to the patient by means of the inspiratory path of the connection system than is flowing from the patient by means of the expiratory path of the connection system, since the medical device strictly specifies the procedure of the ventilation and adaptations in reference to the patient's own breathing efforts do not take place. In case of a control of the ventilation with so-called assisted forms of ventilation, in which, for example, the administration of a breath by the medical device is required by the patient, for example, due to a trigger event (Flow Trigger, Pressure Trigger), there are operating states in the ventilation in which a smaller quantity of breathing gas is being fed or flows to the patient by means of the inspiratory path of the connection system than is flowing from the patient by means of the expiratory path of the connection system, in which the medical device with the current state of inhalation or exhalation and the then following breathing phase of the patient at the time of the trigger event are not identical.

For configurations and embodiments for detecting the airway pressure $P_{AW}$, possible measuring sites and hence preferred embodiments for the pressure measurement resulting therefrom appear Table 1.

In a special embodiment of the medical device, the airway pressure $P_{AW}$ is detected and determined by the control unit by means of a pressure sensor arranged at the patient connection path or at the connection component (Y-piece) of the connection system.

In a special embodiment of the medical device, the airway pressure $P_{AW}$ is detected and determined by the control unit by means of a pressure sensor arranged at the inspiratory path of the connection system.

In a special embodiment of the medical device, the airway pressure is detected and determined by the control unit of a pressure sensor arranged at the expiratory path of the connection system.

For configurations and embodiments for detecting the patient flow rate, possible measuring sites and hence preferred embodiments for the flow rate measurement resulting therefrom appear from the compilation according to Table 1.

In a special embodiment of the medical device, the patient flow rate is detected and determined by the control unit by means of a difference of a flow sensor arranged in or at the expiratory path of the connection system and a flow sensor arranged in or at the inspiratory path of the connection system.

In a special embodiment of the medical device, the patient flow rate is detected and determined by the control unit by means of a flow sensor arranged in or at the patient connection path or at the connection component of the connection system.

In a special embodiment of the medical device, the flow sensor is configured as a sensor according to a measurement principle of a differential pressure measurement, as a sensor according to a measurement principle of an ultrasonic flow sensor, as a sensor according to a thermoelectric measurement principle (hot wire sensors, hot film sensors), as sensor according to a resistive measurement principle or as a sensor according to a resistive or thermoelectric measurement principle combined with an analysis of a heat transport.

The pressure sensor is configured as a sensor according to a measurement principle of a piston manometer or of a pressure scale, of a compression liquid manometer, of a spring manometer, of a piezoelectric measuring component or of a strain measuring component in a special embodiment of the medical device.

The present invention is now explained in greater detail by means of the following figures and the corresponding figure descriptions without limitations of the general idea of the present invention. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
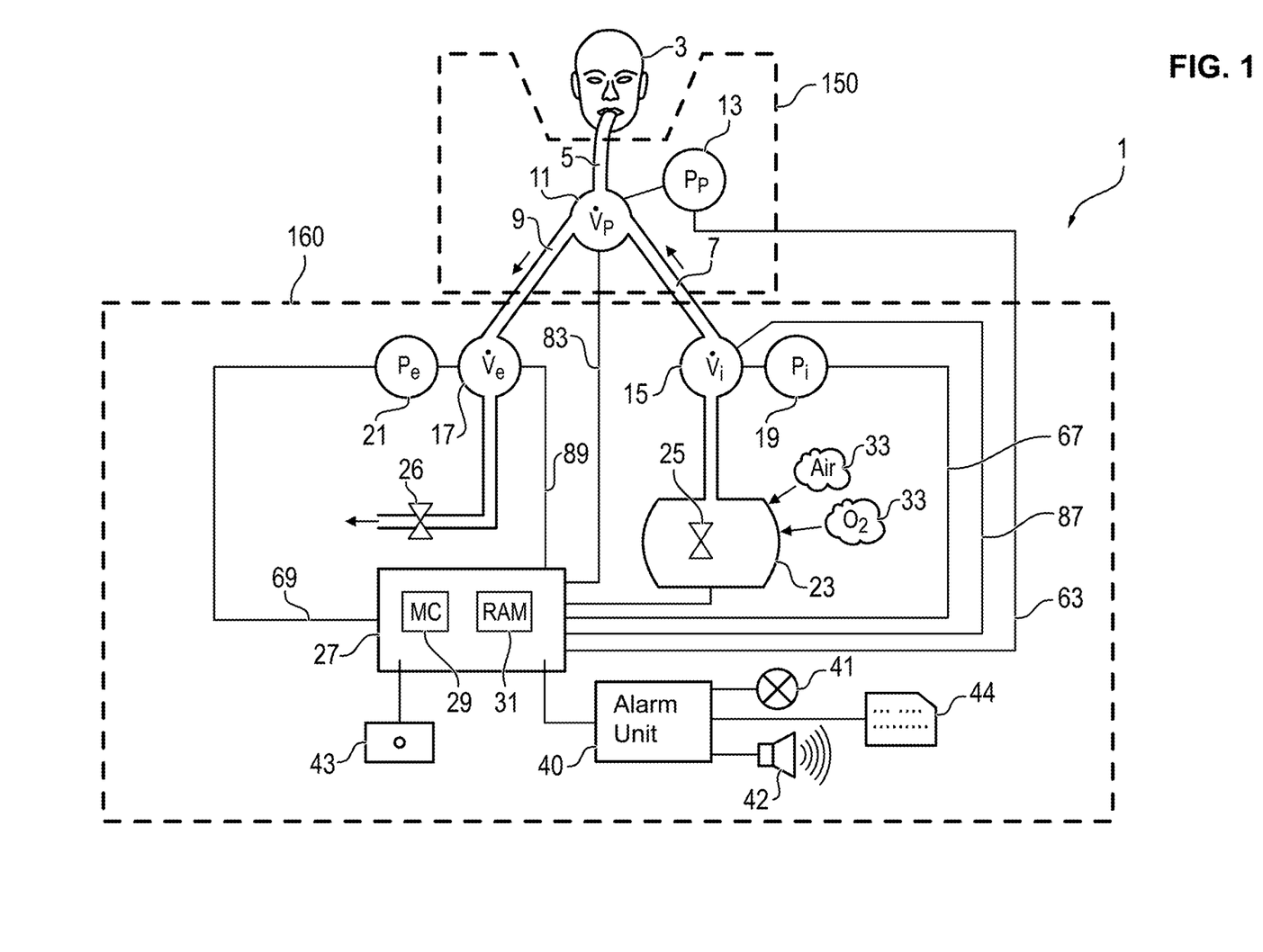
FIG. 1 is a schematic view of a medical device suitably configured for a ventilation.

Referring to the drawings FIG. 1 shows a schematic view of a medical device which is suitably configured for a ventilation, for example and preferably a ventilator with its essential components.

These essential components also represent the basic components of the gas supply, gas dispensing and gas feeding to the patient and for an anesthesia device. The additional, other components that are needed for an anesthesia device, which are not shown in this FIG. 1 and shall also not be listed conclusively at this point, because they do not make any inventive contribution to the present invention for alarm organization in case of a medical device 1, are, for example, gas supply components for dispensing nitrous oxide and anesthetics, gas concentration measurement (anesthesia gas monitoring) for anesthetics and gases, removal of carbon dioxide, and anesthetic gas delivery (AGS). Nevertheless, configurations of the medical device as an anesthesia device, as well as other types of ventilators with different devices for generating and dispensing breathing gas shall also be covered by the view according to FIG. 1. As examples of different devices for generating and dispensing breathing gas, technical configurations with radial flow compressors, blowers, fan impellers, piston drive, valves or nozzles, for example, ejectors or supercritical nozzles, should be mentioned here.

The ventilator 1 has a control unit 27, which is preferably configured as an electronic controller, which is suitably configured and intended to control or regulate a gas mixing and dispensing unit 23 with a dispensing valve arrangement 25 arranged there. Furthermore, measuring sites 15, 17, 19, 21 within the ventilator 1 are shown in the ventilator 1. A measuring site of the inspiratory flow rate 15 and a measuring site for an inspiratory pressure 19 are arranged downstream of the gas mixing and dispensing unit 23. An inhalation branch 17 of a pneumatic connection system, via which the ventilator 1 supplies inspiratory breathing gases to the patient 3, is arranged following these measuring sites 15, 19. A measuring site of a patient flow rate 11 and a measuring site of a patient pressure 13, from which the patient 3 is connected to the ventilator 1 via a patient gas supply line 5, which is usually configured as an endotracheal tube, for the exchange of inhaled and exhaled air, are arranged as connection components at a so-called Y-piece 11 directly at the patient 3, outside 150 of the ventilator 1, but interacting with the ventilator 1.

As an alternative to the endotracheal tube, non-invasive components can also be used for the patient gas supply 5 as a patient connection path, such as masks, for example, nasal masks at the Y-piece. The exhaled air of the patient 3 is fed back by expiration to the ventilator 1 from the Y-piece at the patient 3 via an exhalation branch 9 of the pneumatic connection system. In the ventilator 1, the pressure in the exhalation branch 9 and hence also the pressure present in the lungs of the patient are set by the control unit 27 by means of an exhalation valve 26, which is often also called positive end-expiratory pressure (PEEP) valve. In addition, the control of the ventilation with cyclical changing of inhalation phases and exhalation phases is brought about via the exhalation valve 26 in connection with the control unit 27 in connection with the gas mixing and dispensing unit 23 and the dispensing valve arrangement 25 arranged therein. A measuring site of the expiratory flow rate 17 and a measuring site for an expiratory pressure 21 are arranged downstream of the exhalation branch of the patient gas supply line 9 within or in the interior 160 of the ventilator 1. In alternative and special embodiments of ventilators 1, specially adapted to the application, such as emergency ventilators or ventilators for home, as well as anesthesia devices, which have, besides the components needed for anesthesia devices for an anesthesia, also components for ventilation, the distribution of measuring sites and components (sensors) may be embodied in reference to the components in the interior 160 and outside 150 differing from the embodiment which is shown in a simplified manner in this FIG. 1. Thus, the components 15, 17, 19, 21 may be arranged outside of 150 as well as within 160 the ventilator.

Such embodiments are also covered by the idea of the present invention, but are not shown for the sake of a simplified view and for the sake of clarity. The exhaled air of the patient 3 is discharged from these measuring sites 17, 21 into the surrounding area. The measuring sites 11, 13, 15, 17, 19, 21 and the flow sensors and pressure sensors—but not shown in detail in this FIG. 1 for the sake of clarity—arranged at these measuring sites are each connected to the control unit 27 via suitable signal and data lines 63, 67, 69, 83, 87, 89. In this FIG. 1, a flow measuring unit and a pressure measuring unit—not shown in this FIG. 1 for the sake of clarity—are configured as integrated into the control unit 27. The control unit 27 has, in addition to the flow measuring unit and the pressure measuring unit, suitably configured data processing and conversion units (signal boosting, signal filtering, A/D conversion), which are not shown in this schematic view according to FIG. 1. The control unit 27 has, furthermore, a processor unit 29 and a data storage unit 31, to configure and to execute the procedure of ventilation by and with the ventilator 1. Gases 33 that are needed for the ventilation, such as oxygen and air, are fed to the gas mixing and dispensing unit 23 by means of lines not shown in this FIG. 1 and are converted there into a gas mixture, which is suitable for a ventilation of the patient 3, through the dispensing valve arrangement 25.

An alarm unit 40 with an optical signal generation component 41 and an acoustic signal generation component 42 is connected to the control unit 27 to signal user alarm situations, which may occur during the operation of the ventilator 1, to the user. Furthermore, an output unit 44 for an output in text form or graphic form is arranged at the alarm unit 40 to output notices, alarms and messages to the user. In addition, an input unit 43, via which the user can both carry out settings, such as ventilation parameters, e.g., ventilation rate, tidal volume, ventilation pressures ($P_{insp}$, PEEP) and alarm limits corresponding thereto, such as the maximum permissible airway pressure ($P_{AW\_High}$), volume limits ($M_{vLow}$) at the ventilator 1 and can acknowledge signaled alarm situations, is also connected to the control unit 27.

Figure 2:
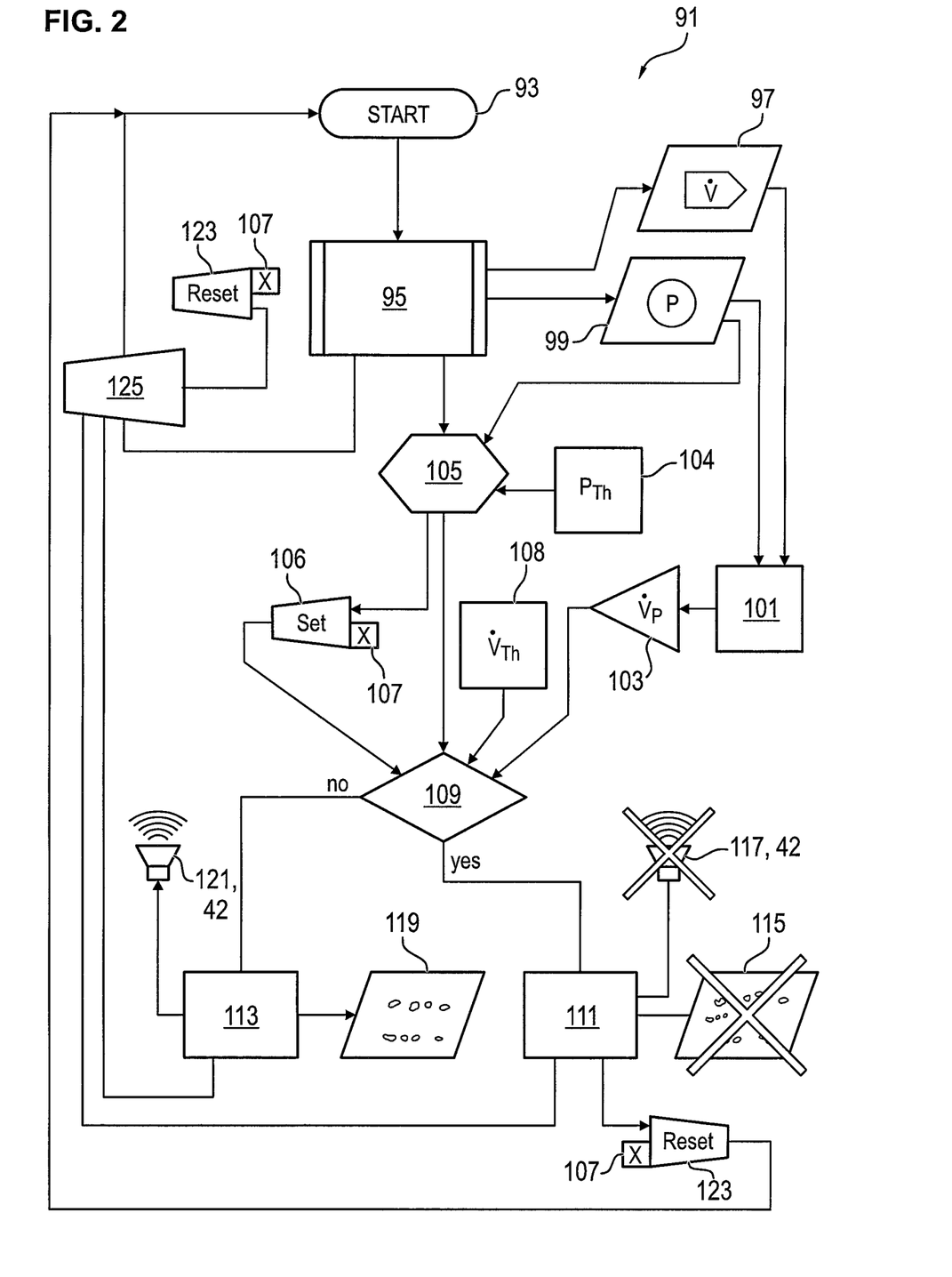
FIG. 2 is a flow chart view of a sequence of actions and steps of an alarm organization.

FIG. 2 shows in a schematic view a sequence of actions and steps of an alarm organization, often also called alarm management or alarm handling. A sequence of actions and steps 91 is shown with a start 93, with an overall function of a ventilation operation 95, as well as other steps and functions in sequence and in conjunction with measured values of the flow 97 and the pressure 99 during the ventilation operation 95. In the regular ventilation operation 95, which is shown here schematically as a function block, pressure measured values 99 and flow measured values 97 are obtained, which are combined in a measured value analysis 101 and are then fed to a patient flow evaluation 103. The patient flow evaluation 103 is executed to assess whether a patient flow is flowing from the patient 3 (FIG. 1) to the ventilator 1 (FIG. 1) at the moment and currently. According to this FIG. 2, a situation with a pressure alarm event 105 arises from the regular and routine ventilation operation 95. This pressure alarm event 105 ($P_{AW\_High}$) is a pressure alarm event, which occurs if the pressure measured values 99 exceed a predefined pressure threshold value 104 and hence the event 105 is considered to be valid. A setting (Set) 106 of a marker 107 for a pressure alarm is brought about due to the event 105.

The flow measured values 97 from the ventilation operation 95 and the pressure measured values 99 from the ventilation operation 95 are provided by the ventilator 1 (FIG. 1). Possible measuring sites or measuring points that are suitable to provide flow measured values and pressure measured values 97, 99, appear from FIG. 1 from the measuring points shown 11, 13, 15, 17, 19, 21 (FIG. 1), which are provided to the control unit 27 (FIG. 1) by signals and data lines 63, 67, 69, 83, 87, 89 (FIG. 1). This control unit 27 (FIG. 1) controls the ventilation operation 95 according to this FIG. 1, as well as the execution of the alarm organization, as it appears, furthermore, from this FIG. 2.

After detecting that a pressure alarm event 105 is present and after setting 106 the marker 107 for the pressure alarm, it is checked in a case differentiation 109 whether the pressure alarm is due to a patient flow in connection with a flow direction with a flow rate flowing from the patient, which exceeds a predefined flow threshold value 108.

An exceeding of the flow threshold value 108 by the patient flow indicates that a coughing event or cough attack has triggered the pressure alarm event 105 ($P_{AW\_High}$).

As a result of this case differentiation 109, the further course of the sequence of steps and actions 91 branches either to a pressure alarm cause 111 which was caused by the patient flow, or to a pressure alarm cause 113 which was not caused by the patient flow. In case of the pressure alarm cause 111, the output of an acoustic pressure alarm 117 is suppressed; a visual alarm output 115 is suppressed as well. In addition, the marker 107 is reset in a resetting step 123. After the suppression of the pressure alarm cause 111, the further operation of the ventilator 1 (FIG. 1) is continued by means of a return to the start 93. In this connection, a branch back is made either directly via a path of a possibility of a manual input and operation 125 of the ventilator 1 (FIG. 1), which is optional and given at any time during the procedure 91, or indirectly to the start 93, in order to again continue the regular ventilation operation 95 from there.

This possibility of a manual input and operation 125 of the ventilator 1 (FIG. 1) given at any time is shown here in this FIG. 2, as an example and in a simplified manner, in the procedure 91 as a component in the branching back to the beginning 93. In a real conversion, the possibility of a manual input and operation 125 is possible by configuring the procedure control almost at any time during the operation of the ventilator 1 (FIG. 1).

In case of a pressure alarm cause 113, i.e., in case the pressure alarm cause 113 was not caused by the patient flow, but, for example, was caused directly by effects of the ventilation control or by an operation or changes of settings of the ventilation controller, an acoustic alarm 121, 42 as well as a visual alarm output 119, 41 (FIG. 1) are outputted. Following the generation of the alarms 113, a branch back is made to the beginning 93 of the sequence of steps and actions 91 via a manual input of an operation of the ventilator 1 (FIG. 1), in which the user acknowledges the alarms, i.e., cancels the marker 107 with a resetting 123.

As an alternative, the resetting 123 of the marker 107 may also be carried out due to the reason for the alarm, i.e., the pressure measured value 99 having again dropped below the threshold value and/or other possible criteria (time criteria, alarm limit settings, configuration of alarm prioritizations) in the procedure 91 being given for the resetting 123. This alternative is not shown in this FIG. 2 for the sake of clarity of the procedure 91. Furthermore, the ventilation operation 95 with the overall function for the operation of the ventilator (FIG. 1) with the continual procedure of the sequence of steps and actions 91, including the alarm organization of the alarm for the elevated airway pressure ($P_{AW\_High}$) 105, is then continued at the beginning 93.

While specific embodiments of the invention have been shown and described in detail to illustrate the application of the principles of the invention, it will be understood that the invention may be embodied otherwise without departing from such principles.

APPENDIX

List of Reference Numbers

1 Medical device arrangement, ventilator
3 Patient
5 Patient gas supply line (pneumatic connection system)
7 Inhalation branch (pneumatic connection system)
9 Exhalation branch (pneumatic connection system)
11 Measuring site for patient flow rate, Y-piece, connection component
13 Measuring site for patient pressure, airway pressure
15 Measuring site for inspiratory flow rate
17 Measuring site for expiratory flow rate
19 Inspiratory pressure, measuring site
21 Expiratory pressure, measuring site
23 Gas mixing and dispensing unit
25 Dispensing valve arrangement
26 Exhalation valve
27 Control unit, electronic controller
29 Processor unit
31 Data storage unit
40 Alarm unit, alarm output
41 Optical signal generation component
42 Acoustic signal generation component
43 Input unit
63, 67, 69 Signal/data lines of the pressure measuring sites
83, 87, 89 Signal/data lines of the flow measuring sites
91 Sequence of steps and actions
93 Beginning, start
95 Ventilation operation, overall function
97 Flow measured values from the ventilation operation
99 Pressure measured values from the ventilation operation
101 Analysis of measured values
103 Patient flow evaluation
104 Pressure threshold value
105 Pressure alarm event ($P_{AW}$ High)
106 Setting of the marker for pressure alarm event (Set)
107 Marker for pressure alarm
108 Flow threshold value
109 Case differentiation for cause of pressure alarm
111 Cause of pressure alarm due to patient flow
113 Cause of pressure alarm, e.g., due to ventilation control or operation
115 Alarm with output suppression, visual
117 Alarm with output suppression, acoustic
119 Alarm with alarm output, visual (display screen/indicator light)
121 Alarm with alarm output, acoustic (loudspeaker, alarm sound)
123 Resetting of the marker for pressure alarm event (Reset)
125 Operation of the ventilator, manual input
150 Components arranged outside of the device
160 Components arranged inside of the device

What is claimed is:

1. A process for alarm organization of a medical device, the process comprising the steps of:
   ventilating a patient with the medical device, wherein the medical device comprises a medical ventilator or a medical respiratory device comprising a mixing and dispensing unit with a dispensing valve arrangement to deliver and provide a breathing gas;
   during the ventilation, providing sensor signals of measuring sites of the medical device, wherein the sensor signals indicate pneumatic and/or fluidic physical states of the breathing gas in a gas-routing connection system from and to the patient, and the gas-routing connection system is fluidly connected and coupled to the medical device and to the patient and has a gas-routing configuration for a transport of the breathing gas;
   determining values, based on the sensor signals, of an airway pressure and of a flow rate that are present in the gas-routing connection system as well as a flow direction corresponding to the gas-routing connection system;
   comparing the determined value of the airway pressure, a value of the airway pressure at a given time, to an airway pressure comparison criterion as an airway pressure comparison, wherein the comparison criterion is not an integral comparison criterion for comparison to airway pressure values integrated over a time period, whereby the determined value of the airway pressure exceeding the airway pressure comparison criterion indicates an elevated airway pressure related to a pressure alarm event;
   setting an alarm criterion as an elevated airway pressure alarm state indicating the elevated airway pressure;
   determining whether the gas-routing connection system is in a gas flow state, in which a smaller quantity of the breathing gas is being fed from the medical device toward the patient than the quantity of breathing gas that flows from the patient, based on a flow rate comparison of whether the determined value of the flow rate and the flow direction exceeds a flow rate comparison criterion, wherein a positive determined value of the flow rate indicates one flow direction and a negative determined value of the flow rate indicates another flow direction;
   resetting the alarm criterion to not be the elevated airway pressure alarm state related to the pressure alarm event based on the pressure alarm event being triggered by a coughing event or coughing attack upon:
      the determined value of the airway pressure, the value of the airway pressure at the given time, exceeding the airway pressure comparison criterion; and
      the gas-routing connection system being in the gas flow state at the given time, in which the smaller quantity of the breathing gas is being fed toward the patient than the quantity of breathing gas that flows from the patient based on the flow rate comparison criterion; and
   adapting a visual and/or acoustic output of a warning or of an alarm indicating the elevated airway pressure based on the alarm criterion set as the elevated airway pressure alarm state.

2. A process in accordance with claim 1, wherein the acoustic output of the warning or the alarm is suppressed or muted as the adaptation of the output of the warning or the alarm when the alarm criterion indicating the elevated airway pressure is reset.

3. A process in accordance with claim 1, wherein the visual output of the warning or the alarm is suppressed as the adaptation of the output of the warning or the alarm when the alarm criterion indicating the elevated airway pressure is reset.

4. A process in accordance with claim 1, wherein the visual and/or acoustic output of the warning or alarm is outputted with a time delay as the adaptation of the output of the warning or alarm when the alarm criterion indicating the elevated airway pressure is reset.

5. A process in accordance with claim 1, wherein both the visual and the acoustic output of the warning or alarm is suppressed as the adaptation of the output of the warning or alarm based on the alarm criterion.

6. A process in accordance with claim 1, wherein no visual and/or acoustic output of the warning or the alarm is outputted as the adaptation of the output of the warning or the alarm based on the alarm criterion, when the alarm criterion is no longer functioning or the user has decided that the alarm criterion is obsolete or the alarm criterion indicating the elevated airway pressure is reset.

7. A process in accordance with claim 1, wherein before the setting of the alarm criterion or before the resetting of the alarm criterion, carrying out a check of whether the medical device is being configured or settings for control of the ventilation are being adapted at the medical device and when the medical device is being configured or the settings for control of the ventilation at the medical device are being adapted, not setting the alarm criterion or not resetting the alarm criterion.

8. A process in accordance with claim 1, wherein a detection of a breathing phase and the determination of whether the medical device is in the gas flow state, in which the smaller quantity of the breathing gas is being fed from the medical device toward the patient than the quantity of the breathing gas that flows from the patient, includes:
    considering a state of an exhalation valve; or
    considering a control signal for an exhalation valve; or
    considering ventilation operation data; or
    considering a state of an exhalation valve and a control signal for the exhalation valve; or
    considering a control signal for an exhalation valve and considering ventilation operation data; or
    considering a control signal for an exhalation valve and considering ventilation operation data; or
    considering a state of an exhalation valve and considering a control signal for the exhalation valve and considering ventilation operation data.

9. A medical device with an alarm organization, the medical device comprising:
    a mixing and dispensing unit with a dispensing valve arrangement to deliver and provide breathing gas;
    a gas-routing connection system configured for a transport of the breathing gas, the gas-routing connection system comprising a connection component, an expiratory path configured to carry away an expiratory quantity of the breathing gas from the patient, an inspiratory path configured to bring an inspiratory quantity of the breathing gas of the medical device to the patient, a patient connection path configured to bring the inspiratory quantity of the breathing gas from the medical device to the patient and for carrying the expiratory quantity of the breathing gas away from the patient, wherein the expiratory path and the inspiratory path are connected to one another and to the patient connection path by the connection component;
    a pressure measuring unit comprising at least one pressure sensor, which is arranged in or at the medical device or the gas-routing connection system and is configured to detect a pressure measured value of a pressure that is present in the gas-routing connection system at a given time, and wherein the pressure measuring unit is configured to provide the pressure measured value;
    a flow measuring unit comprising at least one flow sensor arranged in or at the gas-routing connection system or in or at the medical device and configured to detect at least one flow rate measured value and a flow direction of the breathing gas, corresponding to the at least one flow rate measured value in which the breathing gas flows from the patient in the gas-routing connection system or flows from the medical device towards the patient, wherein a positive flow rate measured value indicates one flow direction and a negative flow rate measured value indicates another flow direction, and wherein the flow measuring unit is configured to provide the at least one flow rate measured value indicating the corresponding flow direction;
    an alarm unit; and
    a control unit receiving the pressure measured value and the flow rate measured value indicating the corresponding flow direction, the control unit being configured to:
    compare the pressure measured value with a predefined pressure threshold value, in which the predefined pressure threshold value is not an integral pressure threshold value, and assess, based on the comparison, whether the pressure measured value indicates an elevated airway pressure related to a pressure alarm event;
    activate an alarm criterion upon assessing that the pressure measured value indicates the elevated airway pressure related to the pressure alarm event;
    compare the at least one flow rate measured value with a predefined flow rate threshold value and assess, based on the comparison, whether the at least one flow rate measured value exceeds the predefined flow rate threshold value;
    assess whether the at least one flow rate measured value and the corresponding flow direction indicate that the gas-routing connection system is in a gas flow state, in which a smaller quantity of the breathing gas is being fed toward the patient from the medical device than a quantity of the breathing gas that is flowing from the patient, based on the flow rate comparison of whether the at least one flow rate measured value exceeds a flow rate comparison criterion;
    deactivate the alarm criterion indicating the elevated airway pressure related to the pressure alarm event based on the pressure alarm event being triggered by a coughing event or coughing attack, for a predefined time, when both:
        the pressure measured value at the given time exceeds the predefined pressure threshold value; and
        the gas-routing connection system is in the gas flow state, at the given time, in which the quantity of the breathing gas flowing towards the patient is smaller than the quantity of the breathing gas flowing from the patient; and
    activate the alarm unit for an output of an alerting visual warning or alarm and/or an alerting acoustic warning or alarm, indicating the elevated airway pressure based on the alarm criterion being active.

10. A medical device in accordance with claim 9, wherein the pressure measuring unit comprises the at least one pressure sensor arranged at the patient connection path or arranged at the connection component of the gas-routing connection system or arranged at the inspiratory path of the gas-routing connection system or arranged at the expiratory path of the gas-routing connection system.

11. A medical device in accordance with claim 10, wherein the at least one pressure sensor is one of the following: a piston manometer of a pressure scale, a compression liquid manometer, a spring manometer, a piezoelectric measuring component, or a strain measuring component.

12. A medical device in accordance with claim 9, wherein the airway pressure is determined by the control unit based on the detection with the pressure measuring unit including the at least one pressure sensor arranged in or at the patient connection path or at the connection component of the gas-routing connection system.

13. A medical device in accordance with claim 9, wherein; the flow measuring unit comprises the at least one flow sensor and at least another flow sensor; the at least one flow rate measured value of the at least one flow sensor and an at least one flow rate measured value of the at least another flow sensor is detected and determined by the control unit with the flow measuring unit providing a difference of the at least one flow rate measured value of the at least one flow sensor and the at least one flow rate measured value of the at least another flow sensor; the at least one flow sensor is arranged in or at the expiratory path of the gas-routing connection system and the at least another flow sensor is arranged in or at the inspiratory path of the gas-routing connection system.

14. A medical device in accordance with claim 13, wherein the at least one flow sensor and the at least another flow sensor each are one of the following: a sensor according to an ultrasonic measurement principle, a sensor according to a thermoelectric measurement principle, a sensor according to a resistive measurement principle, or a sensor according to a resistive or thermoelectric measurement principle combined with an analysis of a heat transport.

15. A medical device in accordance with claim 9, wherein the flow rate measured value is detected and determined by the control unit with the flow measuring unit including the at least one flow sensor arranged in or at the patient connection path of the gas-routing connection system.

16. A medical device alarm organization process, the process comprising:
providing a medical device with a mixing and dispensing unit with a dispensing valve arrangement to deliver and provide breathing gas and a gas-routing connection system configured for a transport of the breathing gas, the gas-routing connection system comprising a connection component, an expiratory path configured to carry away an expiratory quantity of breathing gas from the patient, an inspiratory path configured to bring an inspiratory quantity of the breathing gas of the medical device to the patient, a patient connection path configured to bring the inspiratory quantity of the breathing gas from the medical device to the patient and for carrying the expiratory quantity of the breathing gas away from the patient, wherein the expiratory path and the inspiratory path are connected to one another and to the patient connection path by the connection component;
providing a pressure measuring unit comprising at least one pressure sensor, which is arranged in or at the medical device or the gas-routing connection system and is configured to detect a pressure measured value of a pressure that is present in the gas-routing connection system at a given time, and wherein the pressure measuring unit is configured to provide the at least one pressure measured value;
providing a flow measuring unit comprising at least one flow sensor arranged in or at the gas-routing connection system or in or at the medical device and configured to detect at least one flow rate measured value of the breathing gas and a flow direction of the breathing gas corresponding to the at least one flow rate measured value, wherein a positive flow rate measured value indicates one flow direction and a negative flow rate measured value indicates another flow direction and wherein the flow measuring unit is configured to provide the at least one flow rate measured value indicating the corresponding flow direction;
providing an alarm unit;
providing a control unit;
receiving the pressure measured value and the flow rate measured value indicating the corresponding flow direction at the control unit;
with the control unit, comparing the detected pressure measured value with a predefined pressure threshold value, in which the predefined pressure threshold value is not an integral pressure threshold value, to assess, based on the comparison, whether the pressure measured value indicates an elevated airway pressure related to a pressure alarm event;
activating an alarm criterion that indicates the elevated airway pressure related to the pressure alarm event;
with the control unit, comparing the at least one flow rate measured value with a predefined flow rate threshold value;
assessing, based on the comparison of the at least one flow rate measured value with the predefined flow rate threshold value, whether the at least one flow rate measured value exceeds the predefined flow rate threshold value to indicate that the gas-routing connection system is in a gas flow state in which a smaller quantity of the breathing gas is being fed to the patient from the medical device than is flowing from the patient;
with the control unit, deactivating the alarm criterion, based on the elevated airway pressure related to the pressure alarm event being triggered by a coughing event or coughing attack, for a predefined time, when both:
the pressure measured value at the given time exceeds the predefined pressure threshold value; and
the gas-routing connection system is in the gas flow state, at the given time, in which the quantity of the breathing gas flowing towards the patient is smaller than the quantity of the breathing gas flowing from the patient; and
with the control unit, activating the alarm unit for an output of a visual and/or an acoustic warning or alarm indicating the elevated airway pressure based on the alarm criterion being active.

17. A process in accordance with claim 16, wherein the airway pressure is detected and determined by the control unit with the pressure measuring unit including the at least one pressure sensor arranged at the patient connection path or at the connection component of the gas-routing connection system or the pressure sensor arranged at the inspiratory path of the gas-routing connection system and/or the pressure sensor being arranged at the expiratory path of the gas-routing connection system.

18. A process in accordance with claim 16, wherein the airway pressure is detected and determined by the control unit with the pressure measuring unit including the at least one pressure sensor arranged in or at the patient connection path or at the connection component of the gas-routing connection system.

19. A process in accordance with claim 16, wherein; the flow measuring unit comprises the at least one flow sensor and at least another flow sensor; the at least one flow rate measured value of the at least one flow sensor and an at least one flow rate measured value of the at least another flow sensor is detected and determined by the control unit with the flow measuring unit providing a difference of the at least one flow rate measured value of the at least one flow sensor and the at least one flow rate measured value of the at least another flow sensor; the at least one flow sensor is arranged in or at the expiratory path of the gas-routing connection system and the at least another flow sensor is arranged in or at the inspiratory path of the gas-routing connection system.

20. A process in accordance with claim 16, wherein the at least one flow rate measured value is detected and determined by the control unit with the flow measuring unit including the at least one flow sensor arranged in or at the patient connection path of the gas-routing connection system.

* * * * *